United States Patent [19]

Holt

[11] Patent Number: 4,702,110

[45] Date of Patent: Oct. 27, 1987

[54] METHOD AND APPARATUS FOR MEASURING METAL HARDNESS UTILIZING LONGITUDINAL AND TRANSVERSE ULTRASONIC WAVE TIME-OF-FLIGHT

[75] Inventor: Albert C. Holt, Trinidad, Calif.

[73] Assignee: J. A. Green Company, Trinidad, Calif.

[21] Appl. No.: 890,597

[22] Filed: Jul. 25, 1986

Related U.S. Application Data

[63] Continuation-in-part of Ser. No. 746,917, Jun. 20, 1985, Pat. No. 4,602,511.

[51] Int. Cl.$^4$ ............................................. G01M 7/00
[52] U.S. Cl. .......................................... 73/573; 73/78
[58] Field of Search ..................... 73/581, 78, 597, 573

[56] References Cited

U.S. PATENT DOCUMENTS 3,416,365 12/1968 Frederick ............................. 73/597
3,955,404 5/1976 Bickel et al. .

FOREIGN PATENT DOCUMENTS 1173297 8/1985 U.S.S.R. .................................. 73/78

OTHER PUBLICATIONS

"Ultrasonic hardness testing", (*Ultrasonics*/Apr. 1966), pp. 88–91.
"Acoustic Measurements of Stress Fields and Microstructure", (*Journal of Nondestructive Evaluation*), vol. 1, No. 1, 1980.

Primary Examiner—Jerry W. Myracle
Attorney, Agent, or Firm—Townsend & Townsend

[57] ABSTRACT

The present invention is a method and apparatus for measuring the average hardness of a metal. This method capitalizes on the discovery that a longitudinal wave will travel roughly twice as fast as a transverse (shear) wave, the times-of-flight of the two waves are affected to different degrees by hardness, and there is a linear relationship between velocity and hardness. Longitudinal and transverse ultrasonic signals are applied to a first end (face) of the metal. The longitudinal and transverse signals are detected at this same first end of the metal after they are reflected off of the second end (face) of the metal. The time-of-flight for each of the longitudinal and transverse waves is measured. The hardness, H, in the metal is then determined by applying substantially the following equation:

$$H = H_1 + h \frac{(R - R_1)}{R_1} \qquad (1)$$

where:
$H_1$ = known hardness for the hard phase of the metal;
$h$ = a constant for the metal alloy;
$R$ = measured ratio of shear and longitudinal times of transit; and
$R_1$ = known ratio of shear and longitudinal times of transit (or velocity) for the hard phase of the metal.

22 Claims, 2 Drawing Figures

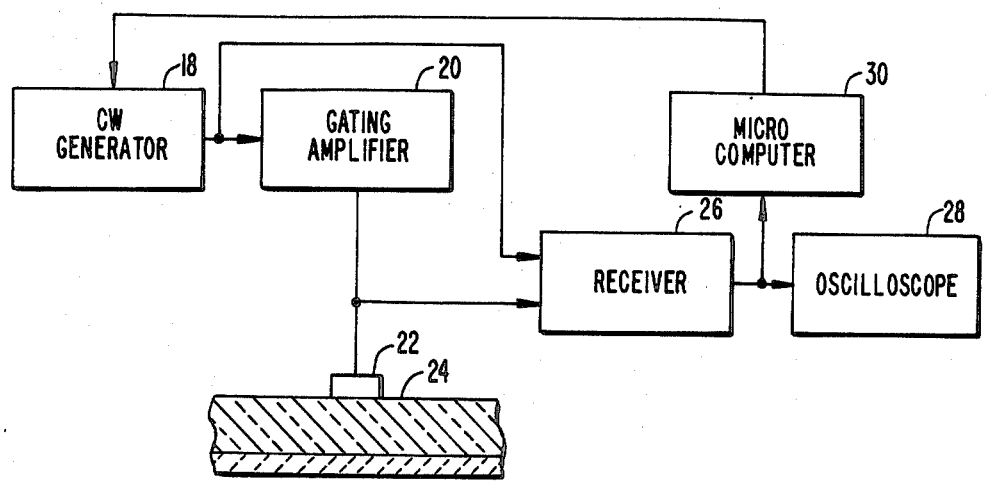
FIG.__1.
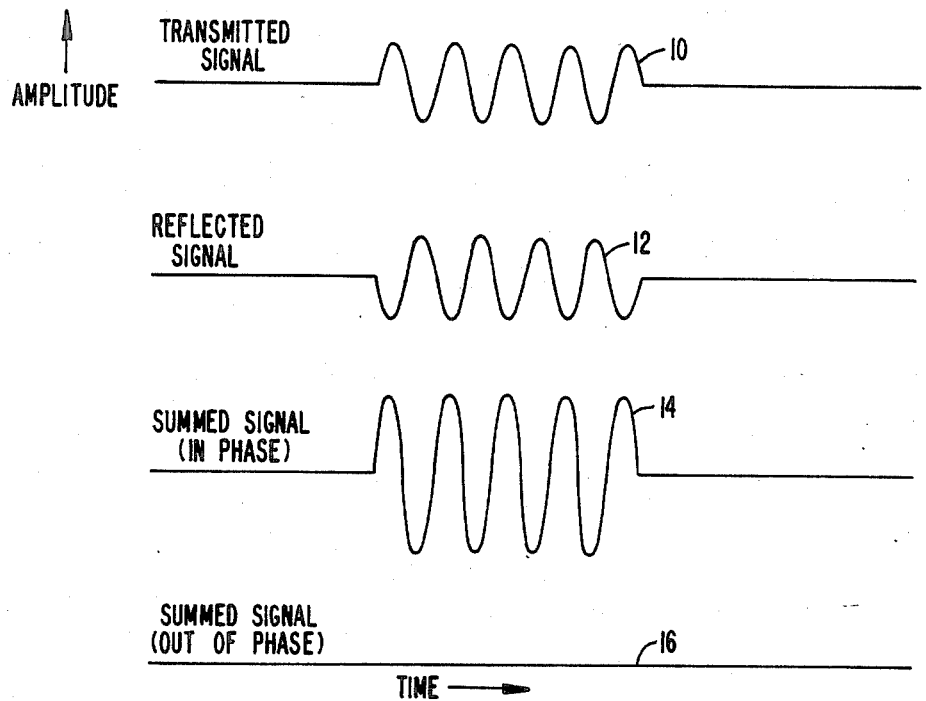
FIG.__2.

METHOD AND APPARATUS FOR MEASURING METAL HARDNESS UTILIZING LONGITUDINAL AND TRANSVERSE ULTRASONIC WAVE TIME-OF-FLIGHT

This is a continuation-in-part of application Ser. No. 746,917 filed June 20, 1985, now U.S. Pat. No. 4,602,511.

BACKGROUND OF THE INVENTION

This invention relates to the measurement of hardness of a metal utilizing ultrasonic signals.

An existing method for measuring hardness in a metal is shown in U.S. Pat. No. 3,955,404 to Bickel, et al. The resonant frequency of a transducer is first measured. The transducer is then placed in contact with the subject metal. The new frequency of oscillation is measured and the difference between the frequencies is determined. A formula is then applied to this frequency difference to determine the hardness of the metal.

In practice, the hardness which is desired to be known is the average hardness of a metal. For any particular alloy (chemical composition) of a metal, several lattice structures are possible with varying amounts of hardness. When the metal is heated and annealed, an attempt is made to achieve a particular lattice structure, or crystalline structure, for that metal. The different structures are often referred to as phases of the metal. The hardness of the various phases or crystal structures is known, but the combination of phases in a particular metal resulting in a combination of hardness values is not known and is the average hardness value which is desired to be measured.

SUMMARY OF THE INVENTION

The present invention is a method and apparatus for measuring the average hardness of a metal. This method capitalizes on the discovery that a longitudinal wave will travel roughly twice as fast as a transverse (shear) wave, the times-of-flight of the two waves are affected to different degrees by hardness, and there is a linear relationship between velocity and hardness. Longitudinal and transverse ultrasonic signals are applied to a first end (face) of the metal. The longitudinal and transverse signals are detected at this same first end of the metal after they are reflected off of the second (face) end of the metal. The time-of-flight for each of the longitudinal and transverse waves is measured. The hardness, H, in the metal is then determined by applying substantially the following equation:

$$H = H_1 + h \frac{(R - R_1)}{R_1} \quad (1)$$

where:
 $H_1$ = known hardness for the hard phase of the metal;
 h = a constant for the metal alloy;
 R = measured ratio of shear and longitudinal times of transit; and
 $R_1$ = known ratio of shear and longitudinal times of transit (or velocity) for the hard phase of the metal.

The time-of-flight can be measured by any number of methods. In one embodiment, the transmitted signal is added to the detected signal and the frequency of the signal is varied until the two signals are out of phase by 180°, thereby giving destructive interference which gives a summed signal of 0. The frequency is then varied to a next adjacent frequency at which the detected and applied signals are 180° out of phase. The time-of-flight, t, can then be determined from the equation:

$$t = 1/(f_1 - f_2)$$

where $f_1$ and $f_2$ are the two adjacent frequencies at which the summed signal is a null. This calculation is carried out separately for the longitudinal and transverse (shear) signals.

A number of time measurements are made and averaged to reduce the error by giving an average time. This is done by determining twenty adjacent frequencies at which destructive interference occurs and dividing the difference between the first and last frequencies by 19.

Preferably, a piezoelectric crystal generates a single signal having longitudinal and transverse components. Because the longitudinal and transverse signals have different times-of-flight, they can be separately monitored at the detecting circuit even though both are generated simultaneously. The pulse length of the generated signal is long enough to enable detection and short enough to ensure that the longitudinal reflected pulse does not overlap the transverse pulse when they are detected.

For a fuller understanding of the nature and advantages of the invention, reference should be made to the ensuing detailed description taken in conjunction with the accompanying drawings.

BRIEF DESCRIPTION OF THE DRAWINGS

FIG. 1 is a block diagram of a preferred embodiment of the measuring circuit of the present invention; and FIG. 2 is a schematic diagram of the signals used in the present invention.

DETAILED DESCRIPTION OF THE PREFERRED EMBODIMENT

The present invention is a new ultrasonic method for measuring hardness which depends on the existence of two distinct phases in the metal: a soft phase obtained when the metal is annealed and a hard phase obtained when the heated metal is cooled very rapidly (quenched). For example, in AISI type 4140 steel the hard phase is martensite and the soft phase is pearlite. At intermediate cooling rates a mixture of the phases occurs.

Sound velocity, as well as hardness, is different in the two phases. In fact, in samples varying continuously along their length from all martensite (at the hard end) to all pearlite (at the soft end), a linear relationship exists between the longitudinal sound velocity and hardness. See Kino, G.S., et al. "Acoustic Measurements of Stress Fields and Microstructure," Journal of Nondestructive Evaluation, Volume 1 (1980) pp 67-77, incorporated herein by reference.

This linear relationship is given by the equation:

$$V_L = V_{L1} + [(V_{L2} - V_{L1})/(H_2 - H_1)](H - H_1) \quad (2)$$

where:
 H = hardness (Rockwell C);
 $V_L$ is the longitudinal sound velocity; and the subscripts 1 and 2 refer to the values in the hard phase and the soft phase, respectively.

The change in sound velocity is a small, but measurable quantity. By using a similar equation for the shear velocity, but with different constants, the two equations can be combined to give:

$$H = H_1 + h\frac{(R - R_1)}{R_1} \quad (1)$$

where:
$H_1$ = known hardness for the hard phase of the metal;
$h$ = a constant for the metal alloy;
$R$ = measured ratio of shear and longitudinal times of transit; and
$R_1$ = known ratio of shear and longitudinal times of transit (or velocity) for the hard phase of the metal.

My invention consists of using the relationship between hardness and the ratio of the sound velocities to estimate hardness from ultrasonic measurements (Note: Eq.(1) can be written in other more complicated forms when more accurate measurements are to be made.) I measure the time-of-flight for the longitudinal and shear waves propagated through a sample of the material, or reflected from the far face of the sample. The ratio of the two flight times is equal to the ratio of the sound velocities since the sample thickness appears in both the numerator and denominator of the ratio and consequently cancels out. Eq. (1) can then be used to estimate the hardness.

Most methods for measuring hardness determine only the hardness at the surface. My method estimates the average hardness through the thickness of the sample. Kino, et al., suggests using the measurement of longitudinal sound velocity to calculate hardness. Their method requires a separate measurement of the thickness of the sample. This is inconvenient, particularly if one wishes to automate the measurement process.

Equation (1) thus enables the determination of the average hardness through a subject metal. Although the hardness for each of the crystalline phases of the metal is known, the composition of phases in a particular metal is not known and the present invention gives an average hardness value which is an indication of the percentage of each phase in the metal.

Several techniques can be used to measure the round trip time-of-flight, such as pulse arrival, pulse echo overlap, phase detection, or sing-a-round. Alternately, the analog signal is converted to digital form and the interval of time between corresponding points on the signal for successive echoes (time-of-flight) is numerically determined using cross-correlation or other techniques.

The phase detection method will be described because it is easily understood. The phase detection method can be understood by reference to FIG. 2. A transmitted longitudinal or transverse signal 10 consists of a short pulse of a sine wave. A reflected signal 12 is a corresponding pulse which has been reflected off the far end of the metal. These two signals are added together to produce a summed signal. When transmitted signal 10 and reflected signal 12 are in phase, a higher amplitude summed signal 14 is produced. However, when transmitted signal 10 and reflected signal 12 are exactly 180° out-of-phase, one signal will cancel the other, giving a zero amplitude summed signal 16. The condition for this zero amplitude or destructive interference signal (or null) is given by:

$$mt = (n + \tfrac{1}{2})/f$$

where:
$t$ = round trip time-of-flight;
$f$ = ultrasonic frequency;
$n$ = any integer; and
$m$ = the echo that is being detected.

The transmitted signal will bounce back and forth between the two ends of the metal giving 1st, 2nd, 3rd, etc. echoes which decrease in amplitude each time. By varying the frequency to give a sequence of m successive nulls of the summed signal, we then have the equations:

$$mt = (n + \tfrac{1}{2})/f$$

and $$mt = (m + n + \tfrac{1}{2})/f'$$

where $f$ and $f'$ are the first and last frequencies giving nulls.

By subtracting these equations, we obtain the single equation:

$$mt(f' - f) = n$$

or $$t = 1/(f' - f)$$

This equation can thus be used to calculate the desired pulse time-of-flight. The accuracy of the value can be improved by measuring a large number of successive frequencies and determining the average time-of-flight. The frequency need not be recorded except for the first and last frequencies and the resultant frequency difference can be divided by the number of nulls detected less one. These measurements are made independently for the longitudinal and transverse waves. The two times-of-flight thus determined for the longitudinal and transverse waves are plugged into equation (2) to give the hardness.

A measuring circuit according to the present invention is shown in FIG. 1. A continuous wave generator 18 produces a high frequency signal, preferably 5–10 megahertz. The signal from CW generator 18 is applied to a gating amplifier 20. Amplifier 20 amplifies the signal and gates it to give pulses of 1–5 microseconds duration. These pulses are applied by an ultrasonic transducer 22 to a first end (face) of an object metal 24. The reflected pulse is detected by transducer 22 and applied to receiver 26. Receiver 26 also receives the transmitted signal from CW generator 18. These signals are summed in receiver 26 and applied to an oscilloscope 28.

By adjusting the frequency of CW generator 18 until a sequence of nulls are observed on oscilloscope 28, the times-of-flight can be determined as noted earlier. The measurements can either be made manually using oscilloscope 28 or automatically using a microcomputer 30 coupled to receiver 26 and CW generator 18. Microcomputer 30 is programmed with the various required constants and causes a variation of frequencies from CW generator 18 to continue until the desired count of nulls from receiver 26 is detected.

As can be seen by reference to FIG. 1, the transmitted signal received by receiver 26 has a different path length from that of the reflected signal from ultrasonic transducer 22. Accordingly, an adjustment must be made either manually or programmed into microcomputer 30 to correct for the fact that the transmitted signal has a longer path to travel through the wires and gating amplifier 20. It is, of course, desired to compare only the paths through the object metal and back, and not the paths in other circuitry. A method for making such correction is described in an article by Peterson, G. L., Chick, B., and Junker, W., entitled "1975 Ultrasonic Symposium Proceedings," IEEE, Cat. No. 75, CHO 994-4SU, incorporated herein by reference.

In an alternate method, the analog signal is digitized at a high sampling rate, preferably 20 MHz. This is done by an analog-to-digital converter in microcomputer 30. The digital signals for successive echoes are analyzed to determine the time between the echoes. The point on each echo that is compared is the first portion of the echo which has an amplitude of more than five times the background noise. Because only the time between echoes is calculated, the electrical path lengths are identical and are cancelled out, eliminating the need to compensate for different path lengths as in the phase detection method.

Preferably, an ultrasonic transducer 22 is used which produces a signal having both transverse and longitudinal components. Due to the fact that the longitudinal wave travels approximately twice as fast as the transverse (shear) wave, the reflected waves can be separately identified and measured. The longitudinal wave can be envisioned as hitting the face of the metal with a hammer and the transverse or shear wave can be envisioned as a wave going through the metal similar to a wave along a clothesline generated by moving one end of the clothesline up and down. Preferably, a 5-10 megahertz signal is used and gated for a pulse of 1-5 microseconds to give 20-100 cycles. This should give a pulse which is short enough so that successive echoes do not overlap and long enough to enable detection. The pulsing can be done every 0.1-0.5 milliseconds.

Ultrasonic transducer 22 preferably focuses the transmitted signals so that they reflect only from a small center portion of the far end of the metal. Without focusing, errors can arise where the far face of the metal is uneven and the signal will have a different distance to travel depending upon which portion of the far end of the metal it reflects from.

As will be understood by those familiar with the art, the present invention may be embodied in other specific forms without departing from the spirit or essential characteristics thereof. For example, another method rather than phase detection could be used for measuring the time-of-flight of the ultrasonic signal. Accordingly, the disclosure of the preferred embodiment of the present invention is intended to be illustrative, but not limiting of the scope of the invention which is set forth in the following claims.

What is claimed is:

1. A method for measuring average hardness in a metal comprising:
    applying a longitudinal ultrasonic signal to a first end of said metal;
    applying a transverse ultrasonic signal to said first end of said metal;
    detecting said longitudinal and transverse signals at said first end after reflection from a second end of said metal;
    measuring the time-of-flight, $t_1$, taken by said longitudinal signal to travel from said first end to said second end and back;
    measuring the time-of-flight, $t_2$, for said transverse signal to travel from said first end to said second end and back; and
    determining the average hardness in said metal from $t_1$ and $t_2$.

2. The method of claim 1 wherein the average hardness, H, is determined substantially according to the following equation:

$$H = H_1 + \frac{h(R - R_1)}{R_1}$$

(where $H_1$=hardness for a hard phase of said metal, $R = t_2/t_1$, h=a constant and $R_1$=ratio of transverse to longitudinal time-of-flight for said hard phase).

3. The method of claim 1 wherein said steps of measuring times $t_1$ and $t_2$ each comprise the steps of
    converting said detected signal into digital form;
    determining corresponding points on successive echoes of said digital signal; and
    determining the amount of time between said corresponding points.

4. The method of claim 1 wherein said steps of measuring times $t_1$ and $t_2$ each comprise the steps of:
    determining a frequency $f_1$ where said detected signal is out of phase with said applied signal by approximately 180°;
    determining a second frequency $f_2$ of said signal, $f_2$ being the next adjacent frequency at which said detected signal is out of phase with said applied signal by approximately 180°; and
    determining the time-of-flight from the frequency difference according to the equation $t = 1/(f_1 - f_2)$.

5. The method of claim 4 wherein said steps of determining frequencies $f_1$ and $f_2$ each comprise the steps of:
    adding said applied signal to said detected signal after reflection; and
    varying the frequency of said signal until the sum of said applied and detected signals is approximately zero.

6. The method of claim 4 further comprising the step of averaging a plurality of frequency difference determinations.

7. The method of claim 6 further comprising the steps of:
    generating said sinusoidal signals; and
    amplifying said sinusoidal signals.

8. The method of claim 7 further comprising the step of compensating for the difference in paths travelled by said applied and said detected signals outside said metal.

9. The method of claim 1 wherein said signals are sinusoidal with a frequency of 5-10 MHz and further comprising the step of gating said signals to produce pulses of 1 to 5 microseconds duration.

10. The method of claim 1 further comprising the step of focusing said signals so that they are reflected from a center portion of said second end of said metal.

11. The method of claim 1 wherein said longitudinal and transverse signals are simultaneously applied to said first end of said metal.

12. An apparatus for measuring hardness in a metal comprising:
    means for applying a longitudinal ultrasonic signal to a first end of said metal;
    means for applying a transverse ultrasonic signal to said first end of said metal;

means for detecting said longitudinal and transverse signals at said first end after reflection from a second end of said metal;

means for measuring the time-of-flight, $t_1$, taken by said longitudinal signal to travel from said first end to said second end and back;

means for measuring the time-of-flight, $t_2$, for said transverse signal to travel from said first end to said second end and back; and means for determining the average hardness of said metal from $t_1$ and $t_2$.

13. The apparatus of claim 12 wherein the average hardness, H, is determined substantially according to the following equation:

$$H = H_1 + \frac{h(R - R_1)}{R_1}$$

(where $H_1$=hardness for a hard phase of said metal, $R = t_2/t_1$, h=a constant and $R_1$=ratio of transverse to longitudinal time-of-flight for said hard phase.)

14. The apparatus of claim 12 wherein said means for measuring times $t_1$ and $t_2$ comprises:
   means for converting said detected signals into digital form; and
   processor means for determining the amount of time between corresponding points on successive echoes of said detected signals.

15. The apparatus of claim 12 wherein said means for measuring times $t_1$ and $t_2$ each comprise:
   means for determining a frequency $f_1$ where said detected signal is out of phase with said applied signal by approximately 180°;

means for determining a second frequency $f_2$ of said signal, $f_2$ being the next adjacent frequency at which said detected signal is out of phase with said applied signal by approximately 180°; and
   means for determining the time-of-flight from the frequency difference according to the equation $t = 1/(f_1 - f_2)$ 16. The apparatus of claim 15 wherein said means for determining frequencies $f_1$ and $f_2$ each comprise:
   means for adding said applied signal to said detected signal after reflection; and
   means for varying the frequency of said signal until the sum of said applied and detected signals is approximately zero.

17. The apparatus of claim 15 further comprising means for averaging a plurality of frequency difference determinations.

18. The apparatus of claim 12 wherein said signals are sinusoidal with a frequency of 5–10 mHz and further comprising means for gating said signals to produce pulses of 1 to 5 microseconds duration.

19. The apparatus of claim 18 further comprising:
   means for generating said sinusoidal signals; and
   means for amplifying said sinusoidal signals.

20. The apparatus of claim 19 further comprising means for compensating for the difference in paths travelled by said applied and said detected signals outside said metal.

21. The apparatus of claim 12 further comprising means for focusing said signals so that they are reflected from a center portion of said second end of said metal.

22. The apparatus of claim 12 further comprising means for applying said longitudinal and transverse signals to said first end of said metal.

* * * * *